| United States Patent [19] | [11] | 4,423,275 |
|---|---|---|
| Myers | [45] | Dec. 27, 1983 |

[54] OLEFIN CONVERSION

[75] Inventor: William H. Myers, Richmond, Va.

[73] Assignee: Ethyl Corporation, Richmond, Va.

[21] Appl. No.: 419,211

[22] Filed: Sep. 17, 1982

[51] Int. Cl.$^3$ .............................................. C07C 6/00
[52] U.S. Cl. ..................................... 585/645; 585/646
[58] Field of Search ................................ 585/645, 646

[56] References Cited

U.S. PATENT DOCUMENTS

| 3,558,518 | 1/1971 | Zuech | 252/429 |
| 3,691,144 | 9/1972 | Zuech | 260/93.1 |
| 4,247,417 | 1/1981 | Banasiak | 252/429 |
| 4,248,738 | 2/1981 | Banasiak | 252/431 |
| 4,269,780 | 5/1981 | Banasiak | 260/405 |

OTHER PUBLICATIONS

Farona, *J. Chem. Soc. Chem. Comm.*, 930–931, (1976).
Greenlee et al., *Inorganic Chemistry*, 15, 2129–2134, (1976).
Grubbs, *Progressive Imorg. Chem.*, 24, 1–50, (1979).
Hogano et al., *Inorganic Synthesis*, 18, 126–131, (1978).
Seyferth et al., *Journal of Organometallic Chemistry*, 229, 275–279, (1982).
Zuech, *J. Chem. Soc. Chem. Comm.*, 1182, (1968).
Zuech, *JACS*, 92, 528–531, (1970).

*Primary Examiner*—Curtis R. Davis
*Attorney, Agent, or Firm*—Donald L. Johnson; John F. Sieberth; Willard G. Montgomery

[57] ABSTRACT

Disproportionation of olefinic hydrocarbons by contact with a catalyst comprising a dicarbonyl(cyclopentadienyl)nitrosyl complex of molybdenum or tungsten and an alkylaluminum halide co-catalyst.

16 Claims, No Drawings

OLEFIN CONVERSION

BACKGROUND

This invention relates to the disproportionation of olefinic hydrocarbons. In one aspect, the invention relates to the disproportionation of olefinic hydrocarbons by contact with a catalyst selected from a Group VIB metal cyclopentadienyl dicarbonyl nitrosyl complex in the presence of an alkylaluminum halide. In another aspect, this invention relates to catalysts for olefin hydrocarbon disproportionation.

The olefin metathesis or disproportionation reaction has been found to be general for a large number of olefins and can be catalyzed by a variety of complexes. By disproportionation or metathesis in this application is meant a reaction in which one or more olefinic hydrocarbon compounds are transformed into other olefins of different molecular weights. More specifically, disproportionation is defined as the conversion of an olefinic hydrocarbon into similar hydrocarbons of higher and lower numbers of carbon atoms per molecule. For example, 1-hexene can be disproportionated to ethylene and 5-decene. The olefinic products of the present invention, for the most part, have established uses such as starting materials for the production of polymers, aldehydes, alcohols and plasticizers.

THE INVENTION

In accordance with the invention, the disproportionation of an olefinic hydrocarbon is accomplished by contacting the hydrocarbon with a catalyst comprising a dicarbonyl(cyclopentadienyl)nitrosyl complex of molybdenum or tungsten and an alkylaluminum halide co-catalyst, preferably ethylaluminum dichloride or ethylaluminum sesquichloride, in a diluent.

Olefins which are subjected to disproportionation according to the process of this invention include olefinic reactants containing at least 2 carbon atoms, preferably from 2 to about 40 carbon atoms, per molecule, and one or more non-conjugated carbon-carbon double bonds.

In general, the olefinic reactants contain one or two non-conjugated carbon-carbon double bonds and are acyclic olefins represented by the formula:

$R_1CH=CHR_2$ wherein $R_1$ and $R_2$ are independently selected from a group consisting of hydrogen, alkyl radicals, alkaryl radicals and alkenyl radicals with each of the radicals containing from 1 to about 18 carbon atoms per radical or a monocyclic olefin represented by the formula:

wherein $R_3$ is an alkylene or alkenylene radical containing from about 3 to about 16 carbon atoms.

Examples of suitable acyclic olefinic reactants include propene, 1-butene, 1-pentene, 2-pentene, 1-hexene, 2-hexene, 1-octene, 2-octene, 4-methyl-1-heptene, 2-nonene, 1-decene, 2-decene, 1-dodecene, 6-dodecene, 1-tetracene, 1-eicosene, 1,4-hexadiene, 4-phenyl-1-butene and 4-phenyl-1-octene. Examples of monocyclic olefins which can be used in the present invention include cyclopentene, cyclooctene, cyclononene, cyclotetradecene, 1,5-cyclododecadiene and 1,6-cyclodecadiene.

The catalyst employed in the invention can be represented by the formula:

$$LM(CO)_2NO$$

wherein $L=(R)_nC_5H_{5-n}$; n is 0–5; R is a monovalent alkyl radical having from 1 to 4 carbon atoms and M=molybdenum or tungsten.

These complexes can be synthesized by following, in general, the published procedures set forth in Hoyano, et al., *Inorganic Synthesis*, 18, 126 (1978). That is, the catalyst complex is prepared by reacting the appropriate cyclopentadienide salt with a Group VIB hexacarbonyl, followed by reaction of the product Group VIB metal cyclopentadienyl tricarbonyl salt with a nitrosylating agent. For example, dicarbonyl(cyclopentadienyl)nitrosyltungsten is prepared by reacting $Na(C_5H_5)$ with $W(CO)_6$ to give $Na[(C_5H_5)W(CO)_3]$ which is then nitrosylated with N-nitroso-p-toluenesulfonamide in tetrahydrofuran.

Specific examples of Group VIB metal cyclopentadiene nitrosyl dicarbonyl complexes which can be used in the practice of the present invention include $(C_5H_5)Mo(CO)_2NO$; $(C_5H_5)W(CO)_2NO$; $(CH_3C_5H_4)Mo(CO)_2NO$; $(CH_3C_5H_4)W(CO)_2NO$; $[(CH_3)_5C_5]Mo(CO)_2NO$ and $[(CH_3)_5C_5]W(CO)_2NO$.

No activity was observed for any of the molybdenum or tungsten complexes without the presence of an alkylaluminum co-catalyst. Co-catalysts suitable for use in the present invention are those alkylaluminum halides of the formulas:

$RAlX_2$ or

$R_3Al_2X_3$ wherein R is a monovalent linear alkyl radical having up to at least four carbon atoms and X=chlorine, bromine or iodine. Preferred co-catalysts are ethylaluminum dichloride and ethylaluminum sesquichloride.

The amount of catalyst employed in the process can be expressed in terms of the molar ratio of olefin to the Group VIB metal cyclopentadiene dicarbonyl nitrosyl complex component. Generally, the molar ratio of olefinic reactant to catalyst complex is in the range of about 1:1 to about 1000:1 and preferably from about 10:1 to about 100:1.

The amount of co-catalyst employed in the process also can range from a molar ratio of about 1:1 to about 1000:1 of olefinic reactant to co-catalyst and preferably ranges from about 10:1 to about 100:1.

The disproportionation reaction can be carried out at temperatures between about 0° C. and 140° C. although temperatures both lower and higher may be used. Preferred reaction temperatures are from about 25° C. to about 100° C.

The pressure during the disproportionation reaction can be subatmospheric, atmospheric or superatmospheric up to about 5000 psig. Preferably, the reaction pressure is from about 5 psig to about 1000 psig.

The use of a solvent for the reaction mixture is not required, though, if desired, a solvent which is inert under the reaction conditions, i.e., those solvents which do not enter into the reaction, may be added to the reaction vessel. Useful solvents which may be used include saturated hydrocarbons, exemplary of which are hexane, octane, cyclohexane; aromatic hydrocarbons, such as benzene or toluene; and halogenated compounds, such as chlorobenzene, chloroform, methylene chloride, bromoform, and the like. Chlorobenzene is a particularly useful diluent.

The amount of diluent can be expressed as a volume ratio of diluent to olefin. Suitable volume ratios of diluent to olefin can be from about 1000:1 to about 1:1000 and preferably from about 20:1 to about 1:5.

In general, reaction time depends on the reaction temperature and pressure and on the particular catalyst system and olefinic reactant used. Generally, a reaction time of from about 0.5 hours to 14 days is suitable, although a reaction time of from about 2 to 24 hours is sufficient to disproportionate the olefinic reactant in the present process.

The olefinic reactants should be dried and free of polar materials prior to being disproportionated. Typically, the reactant material is filtered through silica gel and stored over molecular sieves prior to use or alternatively can be distilled from suitable drying agents.

The reaction product mixture from the disproportionation can be worked up using any combination of conventional separation and purification techniques. Depending on the relative volatilities of the unreacted starting olefins, the olefin products and the diluent, the reaction mixture can frequently be separated by fractional distillation. The unreacted starting olefin and diluent can be recycled to the reaction zone if desired. The olefin products can be purified by conventional techniques such as crystallization, distillation, or extractions.

The olefinic reactants and solvent used in the following examples were commercial materials which were routinely distilled from calcium hydride, de-oxygenated and stored over 4A molecular sieves in a glove box before use. The alkylaluminum halides were commercial materials and were used as received. A nitrogen atmosphere was provided for all of the reactions and manipulations. A nitrogen-flushed glove box was used in this regard.

Each of the runs in the following examples was carried out in an oven-dried 2-dram vial equipped with a stir bar and all reaction solutions were prepared in a nitrogen-flushed glove box. For each run a vial was charged with olefin (substrate), chlorobenzene (diluent), catalyst (added as a solid or a neat liquid) and co-catalyst (added as a chlorobenzene solution). Each vial was then sealed with a teflon-faced silicon rubber septum held in place by an open-top screw cap. After preparation of the reaction solution was completed, it was stirred in the glove box in an aluminum block reactor at 75° C. After 18 hours, the vial was cooled and removed from the glove box. In some cases, a run was repeated at ambient temperature (~25° C.) to check for the effect of variations in temperature. Further, some runs were carried out at the bench so as to allow for the possibility of oxygen incursion into the reaction system. A sample of each reaction solution was removed by syringe and hydrolyzed by the addition of ethanol followed by aqueous ammonia. The organic layer was removed, dried over $MgSO_4$ and analyzed by gas chromatography. Concurrent gas chromotography/mass spectroscopy and/or capillary gas chromotography were used to confirm structure assignments.

EXAMPLE I

A series of runs was carried out involving the disproportionation of 1-hexene in the present of different Group VIB metal cyclopentadiene dicarbonyl nitrosyl catalysts and an alkylaluminum halide co-catalyst. In each run, the reaction vial was charged with 0.2 mL of 1-hexene, 0.8 mL chlorobenzene, 1 to 2 mg of catalyst and 30 μL of a 2.0 molar solution of either ethylaluminum dichloride or ethylaluminum sesquichloride in chlorobenzene. The reaction conditions and results are presented in Table I.

TABLE I

| Run No. | Substrate | Catalyst | Co-Catalyst | Conditions | Temp. | % Substrate | % Metathesis Products | % Isomerized Substrate | % Other Olefins |
|---|---|---|---|---|---|---|---|---|---|
| 1 | 1-hexene | $(C_5H_5)Mo(CO)_2NO$ | $EtAlCl_2$ | dry box | 75° C. | 20.0 | 21.1 | 56.6 | 2.4 |
| 2 | 1-hexene | $(C_5H_5)Mo(CO)_2NO$ | $EtAlCl_2$ | dry box | 75° C. | 22.4 | 13.1 | 64.3 | 0.2 |
| 3 | 1-hexene | $(CH_3C_5H_4)Mo(CO)_2NO$ | $EtAlCl_2$ | dry box | 75° C. | trace | 4.9 | 94.0 | 0 |
| 4 | 1-hexene | $[(CH_3)_5C_5]Mo(CO)_2NO$ | $EtAlCl_2$ | dry box | 75° C. | trace | 0 | 99.9 | 0 |
| 5 | 1-hexene | $(C_5H_5)W(CO)_2NO$ | $EtAlCl_2$ | dry box | 75° C. | 10.1 | 17.0 | 72.5 | 0.2 |
| 6 | 1-hexene | $(CH_3C_5H_4)W(CO)_2NO$ | $EtAlCl_2$ | dry box | 75° C. | 60.6 | 2.0 | 37.4 | 0 |
| 7 | 1-hexene | $[(CH_3)_5C_5]W(CO)_2NO$ | $EtAlCl_2$ | dry box | 75° C. | 82.1 | 0.3 | 17.5 | 0.1 |
| 8 | 1-hexene | $(C_5H_5)Mo(CO)_2NO$ | $EtAlCl_2$ | dry box | 25° C. | 2.6 | 28.8 | 62.5 | 6.0 |
| 9 | 1-hexene | $(C_5H_5)Mo(CO)_2NO$ | $EtAlCl_2$ | dry box | 25° C. | 0 | 31.7 | 57.7 | 10.6 |
| 10 | 1-hexene | $(CH_3C_5H_4)Mo(CO_2NO$ | $EtAlCl_2$ | dry box | 25° C. | 88 | 11.8 | trace | 0 |
| 11 | 1-hexene | $[(CH_3)_5C_5]Mo(CO)_2NO$ | $EtAlCl_2$ | dry box | 25° C. | trace | trace | 99.9 | 0 |
| 12 | 1-hexene | $(C_5H_5)W(CO)_2NO$ | $EtAlCl_2$ | dry box | 25° C. | 50.6 | 36.0 | 13.3 | 0 |
| 13 | 1-hexene | $(CH_3C_5H_4)W(CO)_2NO$ | $EtAlCl_2$ | dry box | 25° C. | 57.1 | 29.5 | 13.4 | 0 |
| 14 | 1-hexene | $[(CH_3)_5C_5]W(CO)_2NO$ | $EtAlCl_2$ | dry box | 25° C. | 92.0 | 2.7 | 5.3 | 0 |
| 15 | 1-hexene | $(C_5H_5)Mo(CO)_2NO$ | $EtAlCl_2$ | bench | 75° C. | 20.4 | 8.8 | 70.7 | 0 |
| 16 | 1-hexene | $(C_5H_5)Mo(CO)_2NO$ | $EtAlCl_2$ | bench | 75° C. | 5.5 | 23.5 | 69.4 | 1.5 |
| 17 | 1-hexene | $(CH_3C_5H_4)Mo(CO)_2NO$ | $EtAlCl_2$ | bench | 25° C. | trace | 29.0 | 71 | 0 |
| 18 | 1-hexene | $[(CJ_3)_5C_5]Mo(CO)_2NO$ | $EtAlCl_2$ | bench | 25° C. | trace | trace | 99.9 | 0 |
| 19 | 1-hexene | $(C_5H_5)W(CO)_2NO$ | $EtAlCl_2$ | bench | 25° C. | 6.0 | 20.9 | 73.1 | 0 |
| 20 | 1-hexene | $(CH_3C_5H_4)W(CO)_2NO$ | $EtAlCl_2$ | bench | 75° C. | 38 | 25.9 | 19 | 16.9 |
| 21 | 1-hexene | $[(CH_3)_5C_5]W(CO)_2NO$ | $EtAlCl_2$ | bench | 75° C. | 83.8 | trace | 16.1 | 0 |
| 22 | 1-hexene | $(C_5H_5)Mo(CO)_2NO$ | $EtAlCl_2$ | bench | 25° C. | 4.1 | 34.9 | 50.4 | 10.5 |
| 23 | 1-hexene | $(CH_3C_5H_4)Mo(CO)_2NO$ | $EtAlCl_2$ | bench | 25° C. | 65 | 34.2 | trace | 0 |
| 24 | 1-hexene | $[(CH_3)_5C_5]Mo(CO)_2NO$ | $EtAlCl_2$ | bench | 25° C. | trace | 0 | 99.9 | 0 |
| 25 | 1-hexene | $(C_5H_5)W(CO)_2NO$ | $EtAlCl_2$ | bench | 25° C. | 75.6 | 24.4 | trace | 0 |
| 26 | 1-hexene | $(CH_3C_5H_4)W(CO)_2NO$ | $EtAlCl_2$ | bench | 25° C. | 85.6 | 14.4 | trace | 0 |
| 27 | 1-hexene | $[(CH_3)_5C_5]W(CO)_2NO$ | $EtAlCl_2$ | bench | 25° C. | 97.7 | 2.3 | trace | 0 |
| 28 | 1-hexene | $(C_5H_5)Mo(CO)_2NO$ | $Et_3Al_2Cl_3$ | dry box | 75° C. | 29.9 | 3.8 | 66.3 | 0 |
| 29 | 1-hexene | $(C_5H_5)Mo(CO)_2NO$ | $Et_3Al_2Cl_3$ | dry box | 25° C. | 91.4 | 8.6 | 0 | 0 |

TABLE I-continued

| Run No. | Substrate | Catalyst | Co-Catalyst | Conditions | Temp. | % Substrate | % Metathesis Products | % Isomerized Substrate | % Other Olefins |
|---|---|---|---|---|---|---|---|---|---|
| 30 | 1-hexene | $(C_5H_5)Mo(CO)_2NO$ | $Et_3Al_2Cl_3$ | bench | 75° C. | 36.4 | 6.5 | 57.1 | 0 |
| 31 | 1-hexene | $(C_5H_5)Mo(CO)_2NO$ | $Et_3Al_2Cl_3$ | bench | 25° C. | 80.2 | 19.8 | 0 | 0 |

The results in Table I indicate that both temperature changes and exposure to oxygen affect the reaction. With some exceptions, it appears that these catalysts work better at lower temperatures. The effect of oxygen is not clear, probably because the extent of oxygen incursion occurring in the experimental runs on the bench was not consistent. In some cases, there appears to be an inhibition of side reactions, and a concomitant slight enhancement of metathesis, but this conclusion is tentative. As an example of this, reference to those runs in Table I where $(CH_3C_5H_4)Mo(CO)_2NO/EtAlCl_2$ was used to catalyze the metathesis of 1-hexene indicates that there is an elimination of isomerization with enhancement of the extent of metathesis as the temperature drops and further enhancement of the extent of metathesis when the reaction is then moved from the glove box to the bench. Metathesis of 1-hexene commonly resulted in both metathesis and isomerization of 1-hexene to other hexenes, probably 2- and perhaps 3-hexene. In most cases, however, there was little evidence of metathesis products arising from the isomerized hexenes. This may suggest that metathesis and isomerization are separate processes catalyzed by different species and that the metathesis phase of the reaction is substantially complete before the onset of significant isomerization.

EXAMPLE II

Another series of runs was carried out involving the process of this invention for the disproportionation of 2-octene in the presence of different Group VIB metal cyclopentadiene dicarbonyl nitrosyl catalysts and an alkylaluminum halide co-catalyst. In this series of experiments, the reaction vial was charged in each run with 0.2 mL 2-octene, 0.8 mL chlorobenzene, 1 to 2 mg of catalyst and 30 μL of a 2.0 molar solution containing either ethylaluminum dichloride or ethylaluminum sesquichloride. The reaction conditions and results are shown in Table II.

TABLE II

| Run No. | Substrate | Catalyst | Co-Catalyst | Conditions | Temp. | % Substrate | % Metathesis Products | % Isomerized Substrate | % Other Olefins |
|---|---|---|---|---|---|---|---|---|---|
| 32 | 2-octene | $(C_5H_5)Mo(CO)_2NO$ | $EtAlCl_2$ | dry box | 75° C. | 43.4 | 56.1 | 0 | 0.5 |
| 33 | 2-octene | $(C_5H_5)Mo(CO)_2NO$ | $EtAlCl_2$ | dry box | 75° C. | 48.9 | 51.1 | 0 | 0 |
| 34 | 2-octene | $(CH_3C_5H_4)Mo(CO)_2NO$ | $EtAlCl_2$ | dry box | 75° C. | 94.3 | 5.7 | 0 | 0 |
| 35 | 2-octene | $[(CH_3)_5C_5]Mo(CO)_2NO$ | $EtAlCl_2$ | dry box | 75° C. | 100 | 0 | 0 | 0 |
| 36 | 2-octene | $(C_5H_5)W(CO)_2NO$ | $EtAlCl_2$ | dry box | 75° C. | 92.7 | 7.3 | 0 | 0 |
| 37 | 2-octene | $(CH_3C_5H_4)W(CO)_2NO$ | $EtAlCl_2$ | dry box | 75° C. | 92.8 | 7.2 | 0 | 0 |
| 38 | 2-octene | $[(CH_3)_5C_5]W(CO)_2NO$ | $EtAlCl_2$ | dry box | 75° C. | 97.9 | 2.1 | 0 | 0 |
| 39 | 2-octene | $(C_5H_5)Mo(CO)_2NO$ | $EtAlCl_2$ | dry box | 25° C. | 57.1 | 42.9 | 0 | 0 |
| 40 | 2-octene | $(C_5H_5)Mo(CO)_2NO$ | $EtAlCl_2$ | dry box | 25° C. | 38.2 | 61.8 | 0 | 0 |
| 41 | 2-octene | $(CH_3C_5H_4)Mo(CO)_2NO$ | $EtAlCl_2$ | dry box | 25° C. | 94.1 | 5.9 | 0 | 0 |
| 42 | 2-octene | $[(CH_3)_5C_5]Mo(CO)_2NO$ | $EtAlCl_2$ | dry box | 25° C. | 99.7 | 0.3 | 0 | 0 |
| 43 | 2-octene | $(C_5H_5)W(CO)_2NO$ | $EtAlCl_2$ | dry box | 25° C. | 61.3 | 38.7 | 0 | 0 |
| 44 | 2-octene | $(CH_3C_5H_4)W(CO)_2NO$ | $EtAlCl_2$ | dry box | 25° C. | 59.9 | 37.6 | 0 | 2.6 |
| 45 | 2-octene | $[(CH_3)_5C_5]W(CO)_2NO$ | $EtAlCl_2$ | dry box | 25° C. | 96.5 | 3.5 | 0 | 0 |
| 46 | 2-octene | $(C_5H_5)Mo(CO)_2NO$ | $EtAlCl_2$ | bench | 75° C. | 68.4 | 31.6 | 0 | 0 |
| 47 | 2-octene | $(C_5H_5)Mo(CO)_2NO$ | $EtAlCl_2$ | bench | 75° C. | 44.2 | 55.8 | 0 | 0 |
| 48 | 2-octene | $(CH_3C_5H_4)Mo(CO)_2NO$ | $EtAlCl_2$ | bench | 75° C. | 95.3 | 4.7 | 0 | 0 |
| 49 | 2-octene | $[(CH_3)_5C_5]Mo(CO)_2NO$ | $EtAlCl_2$ | bench | 75° C. | 99.9 | trace | 0 | 0 |
| 50 | 2-octene | $(C_5H_5)W(CO)_2NO$ | $EtAlCl_2$ | bench | 75° C. | 92.7 | 7.3 | 0 | 0 |
| 51 | 2-octene | $(CH_3C_5H_4)W(CO)_2NO$ | $EtAlCl_2$ | bench | 75° C. 38.6 | 38.5 | 0 | 22.9 | |
| 52 | 2-octene | $[(CH_3)_5C_5]W(CO)_2NO$ | $EtAlCl_2$ | bench | 75° C. | 96.9 | 3.1 | 0 | 0 |
| 53 | 2-octene | $(C_5H_5)Mo(CO)_2NO$ | $EtAlCl_2$ | bench | 25° C. | 40.7 | 59.3 | 0 | 0 |
| 54 | 2-octene | $(CH_3C_5H_4)Mo(CO)_2NO$ | $EtAlCl_2$ | bench | 25° C. | 100 | 0 | 0 | 0 |
| 55 | 2-octene | $[(CH_3)_5C_5]Mo(CO)_2NO$ | $EtAlCl_2$ | bench | 25° C. | 99.8 | 0.2 | 0 | 0 |
| 56 | 2-octene | $(C_5H_5)W(CO)_2NO$ | $EtAlCl_2$ | bench | 25° C. | 90.6 | 9.4 | 0 | 0 |
| 57 | 2-octene | $(CH_3C_5H_4)W(CO)_2NO$ | $EtAlCl_2$ | bench | 25° C. | 98.5 | 1.5 | 0 | 0 |
| 58 | 2-octene | $[(CH_3)_5C_5]W(CO)_2NO$ | $EtAlCl_2$ | bench | 25° C. | 99.3 | 0.7 | 0 | 0 |
| 59 | 2-octene | $(C_5H_5)Mo(CO)_2NO$ | $Et_3Al_2Cl_3$ | dry box | 75° C. | 98.1 | 1.9 | 0 | 0 |
| 60 | 2-octene | $(C_5H_5)Mo(CO)_2NO$ | $Et_3Al_2Cl_3$ | dry box | 25° C. | 88.4 | 11.6 | 0 | 0 |
| 61 | 2-octene | $(C_5H_5)Mo(CO)_2NO$ | $Et_3Al_2Cl_3$ | dry box | 75° C. | 92.4 | 7.1 | 0 | 0 |
| 62 | 2-octene | $(C_5H_5)Mo(CO)_2NO$ | $Et_3Al_2Cl_3$ | bench | 25° C. | 99.4 | 0.6 | 0 | 0 |

Having described the process which Applicant regards as his invention, it should be recognized that changes and variations within the scope and spirit of the invention can be made by one skilled in the art and it is accordingly to be understood that the present description of the invention is illustrative only. It is desired that the invention be limited only by the lawful scope of the following claims.

I claim:

1. A disproportionation process which comprises contacting a suitable olefinic reactant with a catalyst comprising a dicarbonyl(cyclopentadienyl)nitrosyl complex of molybdenum or tungsten and an alkylaluminum halide.

2. The process of claim 1, wherein said olefinic reactants contain from about 2 to 40 carbon atoms and one or more non-conjugated carbon-carbon double bonds per molecule and are either (1) an acyclic olefin of the formula:

$$R_1CH=CHR_2$$

wherein $R_1$ and $R_2$ are independently selected from the group consisting of hydrogen, alkyl radicals, alkaryl radicals and alkenyl radicals where each of said radicals contains 1 to 18 carbon atoms, or (2) a monocyclic olefin represented by the formula:

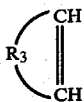

wherein $R_3$ is an alkylene or alkenylene radical containing 3 to about 16 carbon atoms per radical.

3. The process of claim 2 wherein said olefinic reactants are selected from propane, 1-butene, 1-pentene, 2-pentene, 1-hexene, 2-hexene, 1-octene, 2-octene, 4-methyl-1-heptene, 2-nonene, 1-decene, 2-decene, 1-dodecene, 6-dodecene, 1-tetracene, 1-eicosene, 1,4-hexadiene, 4-phenyl-1-butene, 4-phenyl-1-octene, cyclopentene, cyclooctene, cyclononene, cyclotetradecene, 1,5-cyclododecadiene and 1,6-cyclodecadiene.

4. The process of claim 1 wherein said catalyst is a dicarbonyl(cyclopentadiene)nitrosyl complex of molybdenum or tungsten having the formula:

LM(CO)$_2$NO wherein L is $(R)_nC_5H_{5-n}$; n is 0–5; R is a monovalent alkyl radical having from 1 to 4 carbon atoms and M is molybdenum or tungsten.

5. The process of claim 4 wherein said dicarbonyl(cyclopentadiene)nitrosyl catalyst is selected from the group consisting of $(C_5H_5)Mo(CO)_2NO$; $(C_5H_5)W(CO)_2NO$; $(CH_3C_5H_4)Mo(CO)_2NO$; $(CH_3C_5H_4)W(CO)_2NO$; $[(CH_3)_5C_5]Mo(CO)_2NO$; and $[(CH_3)_5C_5]W(CO)_2NO$.

6. The process of claim 1 wherein said alkylaluminum halide is an alkylaluminum halide of the formula:

RAlX$_2$ or

R$_3$Al$_2$X$_3$ wherein R is a monovalent linear alkyl radical having up to at least 4 carbon atoms and X is chlorine, bromine or iodine.

7. The process of claim 6 wherein said alkylaluminum halide is selected from ethylaluminum dichloride or ethylaluminum sesquichloride.

8. The process of claim 1 wherein said disproportionation is carried out in the temperature range of about 0° C. to about 140° C. and under pressure in the range of about 5 psig to about 5000 psig.

9. The process of claim 1 wherein the molar ratio of olefinic reactant to catalyst is in the range of about 1:1 to about 1000:1.

10. The process of claim 1 wherein the molar ratio of olefinic reactant to alkylaluminum halide is from about 1:1 to 1000:1.

11. The process of claim 1 wherein said reaction is carried out in the presence of a diluent.

12. The process of claim 11 wherein said diluent is selected from saturated hydrocarbons, aromatic hydrocarbons and halogenated hydrocarbons.

13. The process of claim 12 wherein said diluent is chlorobenzene.

14. The process of claim 11 wherein the volume ratio of diluent to olefinic reactant is from about 1000:1 to about 1:1000.

15. The process of claim 1 wherein 2-octene is reacted to produce 2-butene and 6-dodecene.

16. The process of claim 1 wherein 1-hexene is reacted to produce ethylene and 5-decene.

* * * * *

UNITED STATES PATENT AND TRADEMARK OFFICE
CERTIFICATE OF CORRECTION

PATENT NO. : 4,423,275

DATED : DECEMBER 27, 1983

INVENTOR(S) : WILLIAM H. MYERS

It is certified that error appears in the above-identified patent and that said Letters Patent is hereby corrected as shown below:

Column 5-6, Table II, Run No. 51, reads across as follows:

"51  2-octene  $(CH_3C_5H_4)W(CO)_2NO$  $EtAlCl_2$  bench  75°C  38.5  0  22.9"
                                                              38.6 and should read across as follows:

-- 51  2-octene  $(CH_3C_5H_4)W(CO)_2NO$  $EtAlCl_2$  bench  75°C  38.6  38.5  0  22.9 --

Signed and Sealed this

Seventeenth Day of April 1984

[SEAL]

Attest:

GERALD J. MOSSINGHOFF

Attesting Officer          Commissioner of Patents and Trademarks